(12) United States Patent
Rødsten

(10) Patent No.: US 6,387,080 B1
(45) Date of Patent: May 14, 2002

(54) METHOD OF FORMING A HYDROPHILIC SURFACE COATING ON A MEDICAL DEVICE AND A MEDICAL DEVICE PREPARED ACCORDING TO THIS METHOD

(75) Inventor: Carsten Bob Rødsten, Sæby (DK)

(73) Assignee: Colorplast A/S

( * ) Notice: Subject to any disclaimer, the term of this patent is extended or adjusted under 35 U.S.C. 154(b) by 877 days.

(21) Appl. No.: 08/784,237

(22) Filed: Jan. 16, 1997

Related U.S. Application Data

(63) Continuation-in-part of application No. 08/182,933, filed on Jan. 18, 1994, now abandoned.

(30) Foreign Application Priority Data

Jan. 21, 1993 (FI) .................................................. 0071/93

(51) Int. Cl.⁷ .......................... A61M 25/00; B32B 27/36
(52) U.S. Cl. ....................................... 604/265; 428/412
(58) Field of Search ................................. 604/265, 266, 604/280, 264; 623/11; 523/105; 424/80; 427/2.1, 2.24, 2.25, 2.28, 2.3; 428/423.7, 424.4, 412

(56) References Cited

U.S. PATENT DOCUMENTS

| 4,585,666 A | * | 4/1986 | Lambert ...................... 604/280 |
| 4,906,237 A | * | 3/1990 | Johansson et al. .......... 604/265 |
| 5,001,009 A | * | 3/1991 | Whitbourne ................ 428/412 |

* cited by examiner

Primary Examiner—Sharon Kennedy
(74) Attorney, Agent, or Firm—Ostrolenk, Faber, Gerb & Soffen, LLP

(57) ABSTRACT

A hydrophilic coating with improved retention of water on a surface, especially a surface of a medical device such as a urethra catheter, prepared by applying on to the surface in a single process step a solution of components that will combine to form the hydrophilic coating, at least one osmolality promoting agent being incorporated into said solution.

14 Claims, No Drawings

METHOD OF FORMING A HYDROPHILIC SURFACE COATING ON A MEDICAL DEVICE AND A MEDICAL DEVICE PREPARED ACCORDING TO THIS METHOD

This application is a continuation-in-part of U.S. patent application Ser. No. 08/182,933, filed Jan. 18, 1994 mow abandoned.

BACKGROUND OF THE INVENTION

The present invention relates to a method of forming an osmolality promoting hydrophilic coating on the surface of a medical device such as a catheter.

It is known to coat medical devices, e.g., catheters for introduction into human cavities such as blood vessels, digestive organs and the urinary system, with a hydrophilic coating, applied as a minimum on that part of the surface which gets into contact with the mucous membranes, etc., during introduction of the device. Whereas such coating in dry condition is not particularly smooth, so that the handling of the device does not become inconvenient, when it is moistened with water immediately before introduction into the human body it becomes extremely slippery, thereby providing a substantially painless introduction.

A large number of methods are known for the production of hydrophilic surface coatings.

These methods are mainly based on the fact that the substrate to be provided with a hydrophilic surface coating, in the course of one or more process stages with intermediary drying and curing, is coated with one or more (mostly two) layers, which are caused to react with one another in different ways, e.g., by polymerization initiated by irradiation, by graft polymerization, by the formation of interpolymeric network structures, or by direct chemical reactions. In this context, reference is made to DK-A-900 855, DK-B-159 018, EP-A-379 156, EP-A-454 293, EP-B2-93 093, GB-A-1 600 963, U.S. Pat. No. 4,119,094, U.S. Pat. No. 4,373,009, U.S. Pat. No. 4,585,666, U.S. Pat. No. 4,666,437, U.S. Pat. No. 4,729,914, U.S. Pat. No. 5,041,100, U.S. Pat. No. 5,001,009 and U.S. Pat. No. 5,120,816, and to WO-A-9005162 and WO-A-9119756.

According to a method known from U.S. Pat. No. 5,001,009, a hydrophilic surface coating is prepared on a substrate by applying, in two stages or in one combined stage, a reactive or an adhesive primer layer and then the actual hydrophilic surface layer, which in that case comprises polyvinylpyrrolidone (PVP) as the active constituent. By this method, there is no chemical reaction between the components of the two layers applied.

Where a device of said type, e.g., a catheter, is to remain inside the body only for some period of time, there may be a risk that water will be extracted from the hydrophilic surface coating and into the body fluids in the surrounding mucous membranes etc., owing to the higher osmotic potential of said body fluids. As a result of the extraction of water, the hydrophilic surface coating will have a tendency to stick to the surrounding tissues, and the removal of the medical device from the body may be painful.

U.S. Pat. No. 4,906,327, the disclosure of which is incorporated herein by reference, describes a method for the production of an enhanced hydrophilic coating with osmolality promoting effect that will maintain the smoothness of the coating for a longer period of time.

According to this method, on a hydrophilic coating prepared by a previously known technique and cured in a separate process stage, applied is an additional and separate coating, consisting of a solution including an agent promoting the osmolality chosen from mono- and disaccharides, sugar alcohols, and nontoxic organic and inorganic salts, after which the solvent is allowed to evaporate. For controlling the viscosity, the solution may also contain a polymer. When drying outside the human body, a surface produced according to this method stays moist longer than conventionally prepared hydrophilic surface coatings, and catheters with a hydrophilic coating enhanced in this way will be easier to remove than those with a conventional coating.

DESCRIPTION OF THE INVENTION

By the present invention, a method of forming a hydrophilic and osmolality promoting coating on the surface of a substrate is provided which for a substrate surface which was not preciously provided with a hydrophilic coating comprises the steps of applying in one process step to the surface of the substrate a solution in a solvent of agents which will combine to form the hydrophilic coating and causing the agents to combine to form the hydrophilic coating wherein an osmolality promoting agent is incorporate into said solution being applied to the substrate such that the osmolality promoting agent is applied to the substrate in the same process step as the solution of agents.

By this method, simpler production and improved stability is achieved in relation to the method known from U.S. Pat. No. 4,906,327, as the osmolality promoting agent, without using an additional, separate coating stage, is included in the solution which the hydrophilic surface coating or its outermost layer is produced. The osmolality promoting agent will often have been dissolved in the same solvent as the components that form the hydrophilic coating, but may also merely be incorporated by emulsification or suspension therein.

By the method according to the invention, the osmolality promoting agent may be any compound that ensures the desired equalization of the difference in osmotic pressures between the moistened coating and the surrounding body fluid. It may thus be chosen from among osmolality increasing electrolytes, e.g., of the same kind as described in U.S. Pat. No. 4,906,327, namely mono- and disaccharides, sugar alcohols, and nontoxic organic or inorganic salts, which may be soluble or insoluble in the solution into which the agent is incorporated. In the method according to the invention, however, the osmolality promoting agent is preferably selected from among urea, amino acids, organic and inorganic acids, and polypeptides and/or mixtures hereof and then incorporated into the solution by dissolution or emulsification.

Urea in this connection shall be understood as urea that has been N-substituted or N,N-disubstituted by lower alkyl.

The substrate onto at least a part of the surface of which the osmolality promoting hydrophilic coating of the inventions is to be applied could be any kind of substrate known in the art for the production of medical articles with hydrophilic coatings. A typical example of a widely used substrate material would be polyvinyl chloride (PVC), but the invention is not limited to the use of this material.

Also for the agents constituting the main constituent for activating the hydrophilic properties of the coating, various materials as disclosed in the art may be used, a typical example being polyvinyl pyrrolidone. However, as disclosed in U.S. Pat. No. 5,001,009 also various types of polyolefines may be used.

In a preferred embodiment of the method, process stages may be employed which, in principle, correspond to those described in U.S. Pat. No. 5,001,009, where a primer is first applied to the substrate, for instance a primer containing nitrocellulose applied in a solution. After drying of the primer layer, an outer layer is applied consisting,e.g., of a solution of polyvinylpyrrolidone in a solvent chosen from among tetrahydrofuran, methylene, chloride, toluene, acetone, a lower aliphatic alcohol, cyclohexanone, $C_2C_4$-alkyl acetates, butyrolactone, and dimethylformamide, of which the most important constituent is ethyl alcohol. However, according to the invention, this solution contains an osmolality promoting agent such as urea in a quantity of 1–20 percent by weight, preferably 2–15 percent by weight and particularly 3–8 percent by weight on the basis of the content of dry polyvinylpyrrolidone.

As explained in the following, testing of the specific combination mentioned above achieved excellent results with a urea quantity within a range of 5–6 percent by weight. For this specific example, it turned out that a significantly lower amount of urea did not give the desired effect with regard to retention of the water used to moisten the coating before introduction of the device.

However, in other combinations than the one specifically stated, there is a likelihood that good results could be achieved also with a quantity of urea outside, i.e. bigger or smaller, than the stated preferred range.

The invention also relates to a medical device for introduction into a body cavity.

Such devices may especially include, in particular catheters, wound drains, and certain surgical instruments. Regardless of the fact that the primary object of this invention is the production of improved catheters for introduction into the urethra in connection with the treatment of dysuria and the achievement of bladder control, the invention may be applied to all such devices intended for the introduction into and withdrawal from a body cavity, whether for human or veterinary use.

For medical device of this type, the invention provides the improvement which comprises incorporation of the osmolality promoting agent into the single hydrophilic coating itself, by being entered into a solution in a solvent of agents used to form the hydrophilic coating.

Example 1 below may serve to illustrate the production of a hydrophilic coating on a catheter based on a polyvinyl chloride (PVC) substrate prepared by the method according to the invention, and through the results of a somewhat schematic field test with different contents of urea as the osmolality promoting agent, the improved maintenance of the smoothness of hydrophilic catheter surfaces prepared according to the invention has been confirmed.

EXAMPLE 1

Four catheters made of PVC were prepared according to a modification of the method described in Example 1 of U.S. Pat. No. 5,001,009 and coated on part of its surface with a hydrophilic coating with improved water retention achieved by first applying a primer layer by immersion into a mixture of 5.4 g of low-viscosity nitrocellulose, 2 g of dibutylphthalate, and 1.9 g of polyvinyl butyral (PVB) in a mixed solution comprising isopropanol, ethyl acetate, ethanol, and acetone (36:13:6:25:18:1.5 V/V). After drying for 5 minutes at 65° C., four catheters primed as described above was provided with an outer layer by immersion into a solution of 6.6 g of polyvinylpyrrolidone and containing 6, 4, 3 or 0 percent w/w of urea, respectively, in relation to polyvinylpyrrolidone in a mixture of ethanol, ethyl acetate, and dimethylformamide (64:23.5:12.5). Finally, the catheters were dried at 65° C. for 60 minutes.

The resistance to removal of the catheters prepared according to this example after conventional catheterization, was assessed by three healthy volunteers (A, B, and C), using the following score system:

| 1 | No resistance |
| 2 | Slight resistance |
| 3 | Great resistance | with the results stated in the table below:

TABLE

| | Urea content, percent by weight | | | |
|---|---|---|---|---|
| Volunteer | 6 | 4 | 3 | 0 |
| A | 1 | 1 | 3 | 3 |
| B | 1 | 1 | 1 | 1 |
| C | 1 | 2 | 3 | 3 |

The results of this schematic test demonstrates that while individual differences in users perception of the degree of comfort or discomfort may play a significant role good results have been achieved at least by one of the test persons throughout the tested urea range of 0 to 6 percent w/w.

This also provides a substantial likelihood that satisfactory result could be achieved even above this range when using other combinations of constituents than those specifically tested.

EXAMPLE 2

A catheter made of PVC was prepared according to a modification of the method described in Example 1 of U.S. Pat. No. 5,001,009 and coated on part of its surface with a hydrophilic coating with improved water retention achieved by first applying a primer layer by immersion into a diluted mixture of 2.2 g of nitrocellulose, 2.1 g of Tecothane TT 2085A-B20 a medical grade aromatic polyurethane and 1.7 g of Tecoflex SG-60D a medical grade aliphatic polyurethane in a mixed solution comprising 94 g toluene, n-butylacetate, Ethylacetate, dibutylphthlate, DL-camphor, 2-hydroxy-4-methoxy-benzophenone, cyclohexanone, 2-butanone, tetrahydrofurane and benzynalcohol (1.1:6.1:3.3:0.6:0.4:0.03:14.9:1.0:71.0:6.0 w/w). The solution was diluted with tetrahydrofurane to a viscosity of 9–13 cP measured with a Hoake type VTO-1 viscometer. After drying for 30 seconds at RT, the catheter primed as described above was provided with an outer layer by immersion into a diluted solution of 7.6 g of polyvinylpyrrolidone and 5.6 percent w/w of urea in relation to the polyvinylpyrrolidone in a mixture of 91.9 g ethanol and butylacetate (81.6:18.4 w/w). The solution was diluted with ethanol and butylacetone (87.5:12.5) to a viscosity of 60–70 cP measured with a Haake type VTO-1 viscometer. Finally, the catheter was dried at 70° C. for 60 minutes.

What is claimed is:
1. In a method of forming a hydrophilic and osmolality promoting agent coating on the surface of a substrate which was not previously provided with a hydrophilic coating comprising applying, in one process step, a solution of agents which will combine to form the hydrophilic coating to the surface of the substrate and causing said agents to combine to form the hydrophilic coating, the improvement which comprises;

incorporating into said solution at least one osmolality promoting agent whereby the osmolality promoting agent is applied to the substrate in the same process step as said solution of agents.

2. A method as claimed in claim 1, wherein the osmolality promoting agent comprises an osmolality increasing electrolyte.

3. A method as claimed in claim 1, wherein the osmolality promoting agent is selected from the group consisting of urea, amino acids, organic and inorganic acids, polypeptides and mixtures thereof, and is incorporated into said solution by dissolution or emulsification therein.

4. A method as claimed in claim 3, wherein said solution comprises polyvinylpyrrolidone or a derivative thereof, and the osmolality promoting agent in the solution comprises urea in a quantity of 1–20 percent by weight based on the quantity of dry polyvinylpyrrolidone.

5. A method as claimed in claim 4, wherein said quantity of urea is 2–15 percent by weight.

6. A method as claimed in claim 5, wherein said quantity of urea is 3–8 percent by weight.

7. A method as claimed in claim 1 wherein a primer layer is applied to the substrate prior to application of said solution of agents to improve the adhesion of the hydrophilic coating to the substrate.

8. In a medical device for introduction into a body cavity comprising a substrate having a surface and a single hydrophilic coating disposed on at least part of said surface and also having at least one osmolality promoting agent associated therewith, the improvement which comprises:

said osmolality promoting agent being incorporated in said hydrophilic coating itself.

9. A device as claimed in claim 8, wherein the osmolality promoting agent comprises an osmolality increasing electrolyte.

10. A device as claimed in claim 8, wherein the osmolality promoting agent is selected from the group consisting of urea, amino acid, inorganic or organic acid, polypeptide or mixtures thereof.

11. A device according to claim 10, wherein a hydrophilic layer of the coating A comprises polyvinylpyrrolidone or a derivative thereof and the osmolality promoting agent comprises urea in a quantity of 1–20 percent by weight based on the quantity of dry polyvinylpyrrolidone.

12. A device as claimed in claim 11, wherein said quantity of urea is 2–15 percent by weight.

13. A device as claimed in claim 12, wherein said quantity by urea is 3–8 percent by weight.

14. A device as claimed in claim 8, wherein the medical device is a catheter comprising a thin elongate tubular body and in which the hydrophilic layer is on the outer surface of said body.

* * * * *

UNITED STATES PATENT AND TRADEMARK OFFICE
CERTIFICATE OF CORRECTION

PATENT NO. : 6,387,080 B1
DATED : May 14, 2002
INVENTOR(S) : Carsten Bob Rødsten It is certified that error appears in the above-identified patent and that said Letters Patent is hereby corrected as shown below:

<u>Title page,</u>
Item [73], should read:
-- [73] Assignee: Coloplast A/S --

Signed and Sealed this

Fourth Day of February, 2003

JAMES E. ROGAN
*Director of the United States Patent and Trademark Office*